(12) United States Patent
Gastauer et al.

(10) Patent No.: US 8,813,769 B2
(45) Date of Patent: Aug. 26, 2014

(54) METHOD AND DEVICE FOR DISSOLVING A SOLID CONCENTRATE

(75) Inventors: Paul Gastauer, Hong Kong (CN); Philippe Laffay, Sainte Foy les Lyon (FR); Benoit Luaire, Sourcieux les Mines (FR)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 234 days.

(21) Appl. No.: 13/259,555

(22) PCT Filed: Apr. 16, 2010

(86) PCT No.: PCT/EP2010/055071
§ 371 (c)(1),
(2), (4) Date: Dec. 7, 2011

(87) PCT Pub. No.: WO2010/121972
PCT Pub. Date: Oct. 28, 2010

(65) Prior Publication Data
US 2012/0067428 A1    Mar. 22, 2012

(30) Foreign Application Priority Data

Apr. 23, 2009  (FR) ...................................... 09 52649

(51) Int. Cl.
*G05D 7/00* (2006.01)
*B01F 1/00* (2006.01)
*B01F 5/04* (2006.01)
*A61M 1/16* (2006.01)

(52) U.S. Cl.
CPC ............ *B01F 1/0022* (2013.01); *B01F 5/0413* (2013.01); *A61M 1/1666* (2014.02); *B01F 1/0005* (2013.01); *A61M 1/1656* (2013.01); *B01F 1/0038* (2013.01)
USPC ................. 137/12; 137/2; 137/102; 137/268; 137/888; 137/895

(58) Field of Classification Search
CPC ...................................... B01F 5/0413
USPC ............ 137/1, 2, 12, 88, 102, 268, 888, 895, 137/101.11, 389, 391, 395
See application file for complete search history.

(56) References Cited

U.S. PATENT DOCUMENTS 3,443,590 A * 5/1969 Karlen et al. .................. 422/261
3,476,137 A * 11/1969 Eisendrath ..................... 137/268

(Continued)

FOREIGN PATENT DOCUMENTS

EP       0278100 A2    8/1988
EP       0917881 A2    5/1999

(Continued)

OTHER PUBLICATIONS

International Search Report of PCT/EP2010/055071, mailing date Jul. 26, 2010.

*Primary Examiner* — Kevin Murphy
(74) *Attorney, Agent, or Firm* — Westerman, Hattori, Daniels & Adrian, LLP

(57) ABSTRACT

A device for putting in solution a powdery concentrate includes a liquid supply pipe (10), an extraction pipe (30) with a valve (31), and a transfer pipe (40) connected to a junction point, the transfer pipe being for connecting to a receptacle (50) containing the concentrate. The junction point is in the constriction of a venturi tube (20), the supply pipe (10) being connected to the convergent chamber (21) and the extraction pipe (30) to the divergent chamber (22). If the valve (31) is closed, the liquid leaves the venturi tube through the vacuum tapping to enter the receptacle. When the valve (31) is opened, the liquid leaves the venturi tube through the divergence chamber, causing a pressure drop in the vacuum tapping. The saturated liquid contained in the receptacle is then sucked and entrained by the liquid passing through the venturi.

5 Claims, 2 Drawing Sheets

(56) References Cited

U.S. PATENT DOCUMENTS

Figure 1:
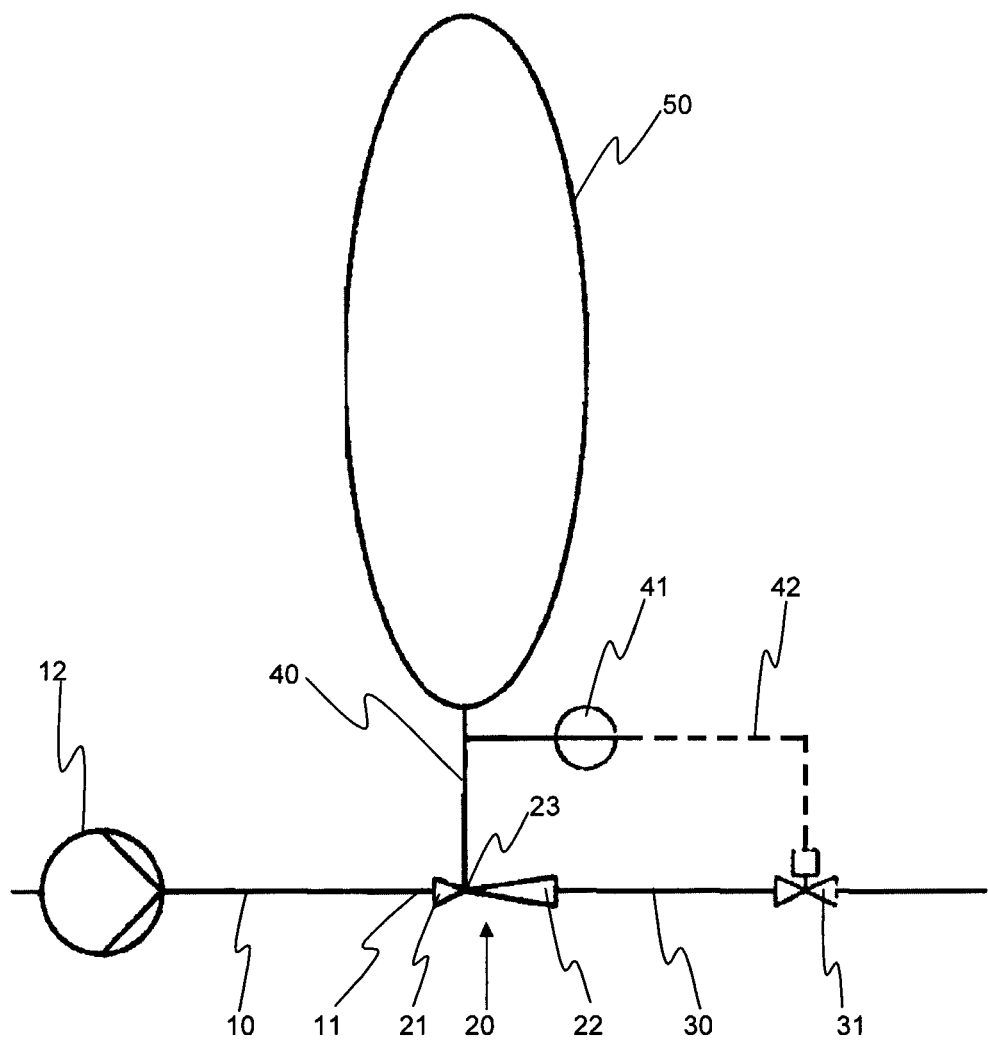

| | | | | |
|---|---|---|---|---|
| 3,872,879 A | * | 3/1975 | Green | 137/268 |
| 4,068,681 A | * | 1/1978 | McNair et al. | 137/588 |
| 4,357,953 A | * | 11/1982 | Patterson | 137/88 |
| 4,908,190 A | * | 3/1990 | Maglio et al. | 422/276 |
| 5,143,111 A | * | 9/1992 | Durbin | 137/100 |
| 6,221,321 B1 | | 4/2001 | Fleischer et al. | |
| 6,230,987 B1 | * | 5/2001 | Truong | 239/310 |
| 6,241,884 B1 | * | 6/2001 | Hansen | 210/198.1 |
| 6,571,989 B1 | * | 6/2003 | Jiang | 222/145.7 |
| 6,701,953 B2 | * | 3/2004 | Agosta | 137/268 |
| 7,077,956 B2 | | 7/2006 | Rovatti | |
| 2003/0137897 A1 | * | 7/2003 | Whiteley | 366/163.2 |
| 2004/0217057 A1 | | 11/2004 | Rovatti | |

FOREIGN PATENT DOCUMENTS

| | | | | |
|---|---|---|---|---|
| GB | 1113675 A | | 5/1968 | |
| GB | 2025787 A | | 1/1980 | |
| WO | 2005/053413 A1 | | 6/2005 | |
| WO | WO 2007/140519 | * | 12/2007 | E03C 1/02 |

* cited by examiner

METHOD AND DEVICE FOR DISSOLVING A SOLID CONCENTRATE

The invention concerns a device for putting in solution a concentrate in the powdery state, composed of a liquid supply conduit the first end of which is provided with means for connecting it to a pressurised liquid source and the second end of which is connected to a junction point, an extraction pipe the first end of which is connected to the junction point and which is provided with a valve and a transfer pipe the first end of which is connected to the junction point and the second end of which is provided with means for connecting it to a receptacle containing the concentrate to be solubilised. The invention also concerns a method for putting in solution a concentrate in the powdery state contained in a receptacle provided with a single opening, the said method consisting of causing a liquid coming from a pressurised liquid source to enter the receptacle through an opening and then extracting the solution enriched with product via the same opening by suction.

It is usual in haemodialysis procedures to produce the necessary solutions directly before the treatment, or even during the treatment. These solutions are obtained by solubilising a solid product, referred to as a solid concentrate, with a suitable liquid, generally water obtained by reverse osmosis (RO water). The solid concentrate is in general a soluble powder or a mixture of soluble powders. The solid concentrate is sold in pouches or cartridges provided with couplings for connecting them to the haemodialysis machines. The water is introduced into the receptacle and becomes loaded with salt until it reaches saturation. The saturated solution is then extracted from the receptacle and transmitted to a dilution device in which the saturated solution is diluted with water (or the suitable liquid) to the required concentration.

In a first type of machine, the water enters through a first coupling and leaves through a second coupling. This type of device makes it possible to obtain the saturated solution continuously. Such a device is described for example in the document EP 0 278 100 A2 or in the document U.S. Pat. No. 7,077,956 B2. In the latter case, the device is provided with a venturi tube for siphoning the cartridge at the end of the dialysis procedure. The main inlet of the venturi tube is connected to the water source via a discharge pipe provided with a first valve. The vacuum tapping of the venturi tube is connected to a second discharge pipe connected to the outlet of the cartridge. A second valve closes this second discharge conduit. During the solubilising procedure, the two discharge pipes are closed and the water enters the cartridge through the top while the saturated solution is sucked by a pump through the bottom of the cartridge. At the end of the procedure, the pump is turned off and the two discharge valves are opened. The water coming from the water source passes through the venturi tube, sucking the rest of the solution contained in the cartridge. The outlet of the venturi tube emerges in a reservoir. This discharge device does not enable the solid concentrate to be put in solution.

In a second type of machine, the extraction of the saturated solution is effected by the same coupling as the supply of water. Such a device is known for example from the document EP 0 917 881 A2. This device makes it possible to produce successive loads of saturated solution until the solid concentrate is exhausted. This device is however particularly complicated. It comprises a pipe supplying water emerging at a junction point from which there start firstly an extraction pipe and secondly a transfer pipe. Each of these pipes is provided with a valve. The supply pipe is connected to a source of water while the extraction pipe leads to a dilution device. An additional pipe connects the source of water to the dilution device.

In a favoured embodiment of the invention, the supply pipe is connected to a pressurised supply system. Firstly, the valve of the extraction pipe is closed while the other two valves are opened. The pressurised water therefore passes through the supply pipe, the junction point and the transfer pipe before entering the receptacle. A sensor determines the moment when the receptacle is full and therefore the end of the filling step. The control unit then closes the valve of the supply pipe and opens the valve of the extraction pipe. A pump situated in the dilution unit is started up and the saturated solution contained in the receptacle is aspirated. If the supply pipe is not connected to a pressurised water source, it is then necessary to provide a pump. The document provides for using a piston pump situated in a fourth pipe emerging at the junction point. The valve situated in the supply pipe and the valve situated in the transfer pipe are then closed alternately to enable firstly the filling of the piston with water and then the injection of the water into the receptacle. This device is therefore particularly complicated and requires at least two valves and a pump for sucking the saturated liquid.

The objective of the invention is therefore to simplify the device presented above in order to facilitate control thereof and to reduce the number of parts therein and the risk of malfunctioning.

This objective is achieved according to the invention because the junction point is placed in the constriction of a venturi tube, the supply pipe being connected to the convergent chamber, the extraction pipe to the divergent chamber and the transfer pipe to the vacuum tapping starting from the constriction of the venturi tube. Here, only the extraction pipe is provided with a valve. Thus, when the pressurised liquid supply pipe is connected, if the valve is closed the liquid enters the venturi tube through the convergence chamber (the main entry to the venturi tube) and, since it cannot leave through the divergence chamber (the exit from the venturi tube) because of the closed valve, leaves again through the vacuum tapping starting transversely from the constriction. It then passes through the transfer pipe and enters the receptacle, where it takes on the product to be dissolved to saturation. When the valve is opened, the liquid coming from the source enters the convergence chamber, passes through the constriction and leaves again through the divergence chamber, causing a pressure drop in the vacuum tapping. The saturated liquid contained in the receptacle is then aspirated and entrained by the liquid passing through the venturi. When the receptacle is empty of liquid, solid concentrate remains. The valve is closed again and the cycle is recommenced. The device according to the invention requires only one valve. With the venturi tube, which requires no electricity supply or any control device, it is no longer necessary to provide a pump specifically intended for the suction of the saturated liquid.

When the device is intended to be connected to a source of liquid at atmospheric pressure, it is preferable to place a pump in the supply pipe. Thus the liquid can be taken off from a reservoir.

To allow automation of the process, it is preferable to provide means for measuring the degree of filling of the receptacle with liquid. It will then be possible to provide means for controlling the opening or closing of the valve according to a signal emitted by the means of measuring the degree of filling of the receptacle with liquid. In a favoured embodiment of the invention, the means of measuring the degree of filling of the receptacle with liquid consist of a pressure sensor disposed in the transfer pipe. This pressure sensor will make it possible to determine firstly the moment when the receptacle is full of liquid during the first part of the cycle and secondly the moment when all the liquid has been sucked out during the second part of the cycle.

In the method according to the invention, the liquid is introduced into the receptacle, passing through a venturi tube, the liquid entering through the convergent chamber of the said tube and emerging through the vacuum tapping of the said tube, before entering the receptacle, and the suction of the enriched solution is obtained by circulating the pressurised liquid in the venturi tube between the convergent chamber and the divergent chamber of the venturi tube.

In order to automate the method, provision is made for determining the end of the filling of the receptacle with liquid and/or the end of suction of the enriched solution. This determination is preferably carried out by measuring the pressure between the vacuum tapping of the venturi tube and the receptacle. It is then possible, in order to cause the suction of the enriched solution, to control the flow of the liquid through the venturi tube according to the state of filling of the receptacle. The flow of the liquid through the venturi tube can be triggered when the receptacle is filled with the liquid and/or the flow of the liquid through the venturi tube is stopped when the suction of the enriched solution is completed.

Figure 2:
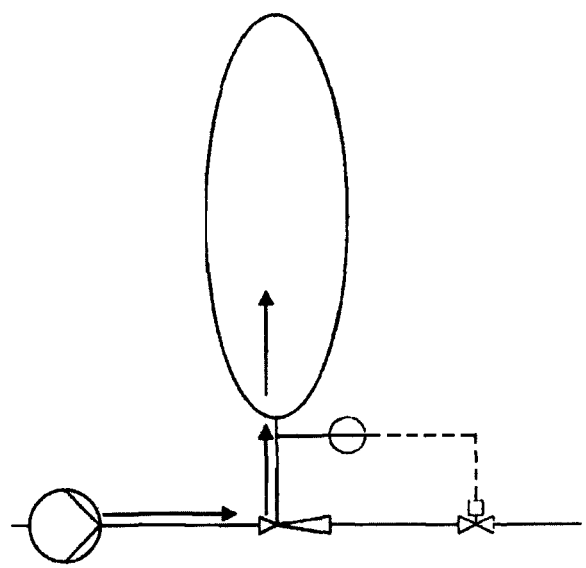

The invention is described in more detail below with the help of the following figures, which show:

FIG. 1: a schematic view of the device;
FIG. 2: the same view during the filling phase; and
FIG. 3: the same view during the extraction phase.

The device of the invention is intended firstly for a haemodialysis machine. It can however be used for any other type of solubilising machine. Hereinafter, reference will generally be made to water, in particular RO water. It goes without saying that any other suitable liquid can be used according to the usage planned.

In the case of haemodialysis, the solution extracted from the receptacle must be a saturated solution. It is however possible that for other applications a non-saturated solution may be desirable. This is why reference is made to a solution enriched with product, this enrichment being able to go as far as saturation.

The device is intended to be connected firstly to a source of liquid, pressurised or not, and secondly to a receptacle containing the solid concentrate. If the source of liquid is not under pressure, the device is provided with a pump so that at the pump outlet there is a pressurised liquid source. The outlet of the device is intended to be connected for example to a dilution unit of the haemodialysis machine.

The device consists of a pressurised water supply pipe (10) one of the ends (11) of which is connected to the inlet (21) of a venturi tube (20). The second end is provided with means for connecting it to a source of liquid. The outlet (22) of the venturi tube (20) is connected to the first end of an extraction pipe (30) in which a valve (31) that may be open or closed is inserted.

The vacuum tapping (23) of the venturi tube (20) is connected to the first end of a transfer pipe (40). The second end of the transfer pipe (40) is provided with means for connecting it to the coupling of a receptacle (50) containing a solid concentrate.

To allow automation of the solubilisation process, it is preferable to provide means for measuring the degree of filling of the receptacle with liquid during filling with the RO water and during the suction of the saturated liquid. Similarly, it is preferable to provide control means for controlling opening or closing of the valve according to predefined parameters, in particular according to the degree of filling of the container. In the example presented here, the means for measuring the degree of filling of the container with liquid consist of a pressure sensor (41) placed in the transfer pipe (40). These measurement means serve to control the valve (31) via the control line (42). They supply the necessary signal to the means for controlling opening or closing of the valve.

The water supply to the device can be done by means of a distribution system having a certain pressure, for example 1.3 bars. It is also possible to have recourse to a source of water such as an RO water pouch and to use a pump (12) placed in the supply pipe (10).

The device of the invention functions as follows. In a first step shown in FIG. 2, the RO water is introduced into the receptacle (50). For this purpose, the valve (31) is closed and the pump (12) started. The water passes through the supply pipe (10), enters the venturi tube (20) through its inlet (21) and emerges from it through the vacuum tapping (23), passes through the transfer pipe (40) and enters the receptacle (50). Depending on the model, this first step is considered to be completed after a certain lapse of time considered to be sufficient to fill the receptacle (50). In the case of the example shown in the figures, this first step is completed when the pressure measured by the sensor (41) in the transfer pipe (40) has reached a first threshold value. During this step, the water passes through the solid concentrate situated at the bottom of the receptacle and becomes loaded with this product to saturation.

Figure 3:
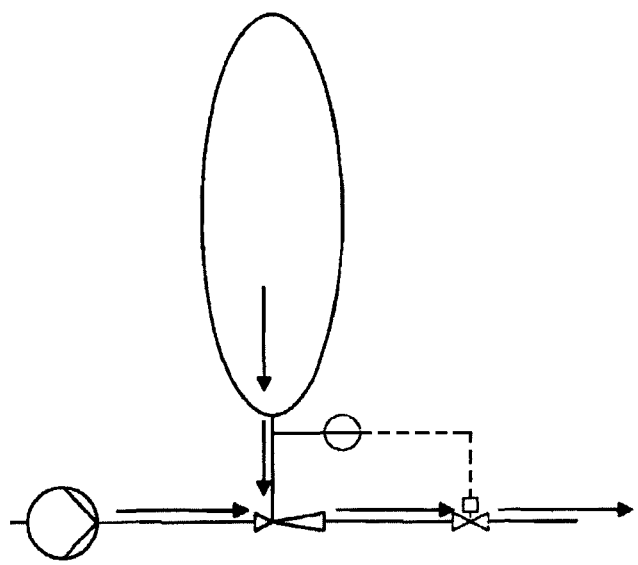

Once this first step is completed, the second step is performed as shown in FIG. 3. The valve (31) is opened, thus enabling the pressurised water coming from the supply pipe (10) to pass through the venturi tube (20). The flow of water through the venturi tube (20) causes a pressure drop at the vacuum tapping (23). The saturated solution in the receptacle is then sucked rapidly and practically completely via the vacuum tapping (23) and is thus mixed with the RO water coming from the inlet (21) of the venturi tube (20). As soon as the receptacle is empty, the valve (31) is closed again and the cycle recommences. The end of the suction of the saturated liquid is measured for example by means of the pressure sensor (41) which, as soon as the pressure in the transfer pipe (40) passes below a second threshold value, demands the closure of the valve (31).

This device is much simpler than the devices of the prior art. It requires only one valve, which can be automated by virtue of means of measuring the degree of filling of the receptacle with liquid. If the device is connected to a water supply system having sufficient pressure, it is not necessary to provide a pump. If the supply water is not under pressure, a single pump suffices.

The invention claimed is:

1. Method for putting in solution a concentrate in the powdery state contained in a receptacle provided with a single opening, the method comprising:
   causing a liquid coming from a source of liquid to enter the receptacle through the single opening, and then
   extracting an enriched solution of the concentrate in the liquid via the same single opening by suction,
      wherein the liquid is introduced into the receptacle by passing through a venturi tube comprising a convergent chamber, a vacuum tapping and a divergent chamber, the liquid entering the tube through the convergent chamber of the tube and leaving the tube through the vacuum tapping of the tube, before entering the receptacle,
      wherein the suction of the enriched solution is obtained by causing pressurised liquid to flow in the venturi tube between the convergent chamber and the divergent chamber, measuring the pressure between the vacuum tapping of the venturi tube and the receptacle by means of a pressure sensor, and controlling opening and closing of a valve according to the degree of filling the receptacle as a function of a pressure signal supplied by the pressure sensor to the valve via a control line, the valve being disposed in an extraction pipe a first end of which is connected to the divergent chamber of the venturi tube.

2. Method according to claim 1, wherein the end of the filling of the receptacle with liquid and/or the end of the suction of the enriched solution are determined according to the pressure measured by the pressure sensor.

3. Method according to claim 2, wherein the flow of liquid through the venturi tube is triggered when the receptacle is filled with the liquid and/or the flow of the liquid through the venturi tube is stopped when the suction of the enriched solution is complete.

4. Device for putting in solution a concentrate in a powdery state contained in a receptacle provided with a single opening, said device comprising:

a liquid supply conduit a first end of which is connected to a liquid source and a second end of which is connected to a junction point;

an extraction pipe a first end of which is connected to the junction point and which is provided with a valve;

a transfer pipe a first end of which is connected to the junction point and a second end of which is connected to the receptacle containing the concentrate to be solubilized;

a pressure sensor for measuring a pressure in the transfer pipe, said pressure sensor being disposed in the transfer pipe and connected to the valve via a control line, and a venturi tube comprising a constriction, a convergent chamber, and a divergent chamber, wherein the junction point is placed in the constriction of the venturi tube, the supply pipe being connected to the convergent chamber, the extraction pipe to the divergent chamber and the transfer pipe to the constriction, wherein the valve is open or closed according to the degree of filling of the receptacle as a function of a pressure signal supplied by the pressure sensor to the valve via the control line.

5. Device according to claim 4, wherein a pump is placed in the supply pipe.

* * * * *